United States Patent [19]

Honda

[11] Patent Number: 4,874,426
[45] Date of Patent: Oct. 17, 1989

[54] SURFACE TENSIOMETER AND CONCENTRATION CONTROLLING DEVICE

[76] Inventor: Hajime Honda, 4-1-6, Yamato-cho, Nada-ku, Kobe-shi, Hyogo-ken, Japan

[21] Appl. No.: 250,671

[22] Filed: Sep. 29, 1988

[30] Foreign Application Priority Data

Sep. 29, 1987 [JP] Japan ................ 62-244600

[51] Int. Cl.⁴ .......................... G01N 13/02
[52] U.S. Cl. .......................... 73/64.4; 73/53
[58] Field of Search .................. 73/53, 64.4

[56] References Cited

U.S. PATENT DOCUMENTS 3,848,618  11/1974  Royse .................... 73/438

FOREIGN PATENT DOCUMENTS 2910201  9/1980  Fed. Rep. of Germany ...... 73/64.4
1096542  6/1984  U.S.S.R. .................... 73/64.4

Primary Examiner—John Chapman
Assistant Examiner—Michele Simons
Attorney, Agent, or Firm—Edwin E. Greigg

[57] ABSTRACT

A surface tensiometer including a measurement container having an upper edge opened horizontally and communicated with an end of a connecting pipe, an inlet container having an upper edge opened at a position higher than the upper edge of the measurement container and communicated with the opposite end of the connecting pipe, and a measuring device. The measuring device is operable to measure a height of a highest position of a convex liquid surface statically formed in an equilibrium between an upward force, exerted by a pressure difference due to a height difference between a liquid surface of said measurement container with the liquid surface being raised from the opened upper edge of the measurement container after the liquid introduced from the inlet container reaches and overflows from the measurement container and a liquid surface of the inlet container and a downward force exerted by a surface tension of the raised liquid surface per se. There is also disclosed a concentration control device for controlling a concentration of liquid constant by utilizing the detection of the convex liquid surface by the surface tensiometer.

32 Claims, 5 Drawing Sheets

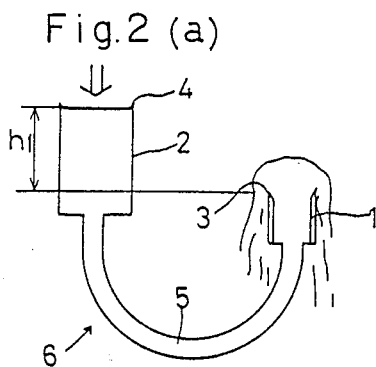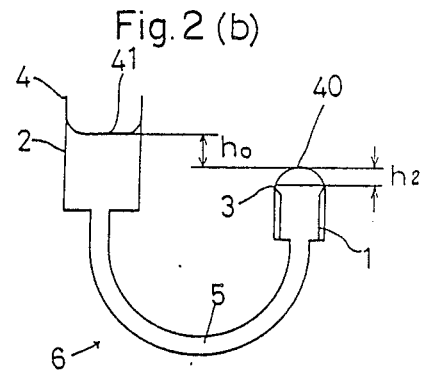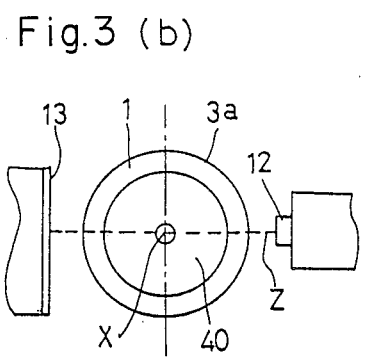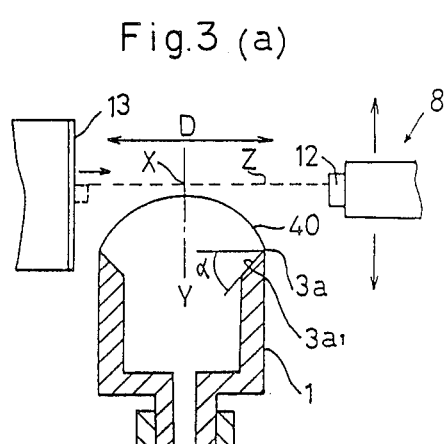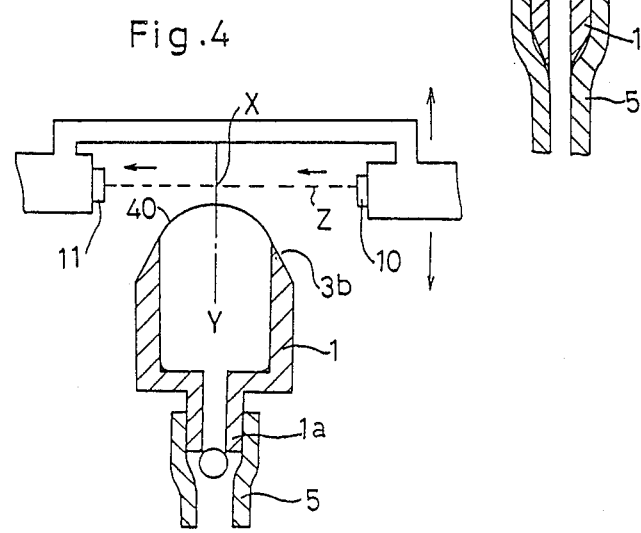

Fig.5 (b)
Fig. 6
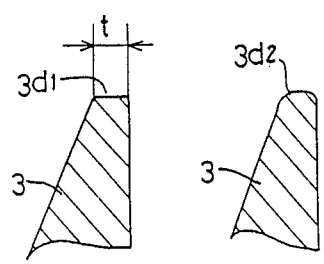
Fig.5(a)
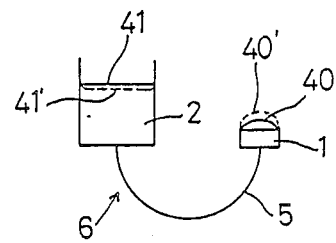
Fig.7
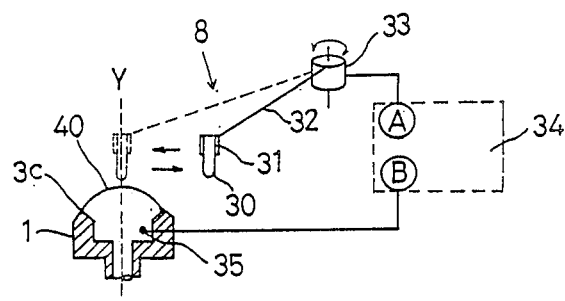
Fig.9
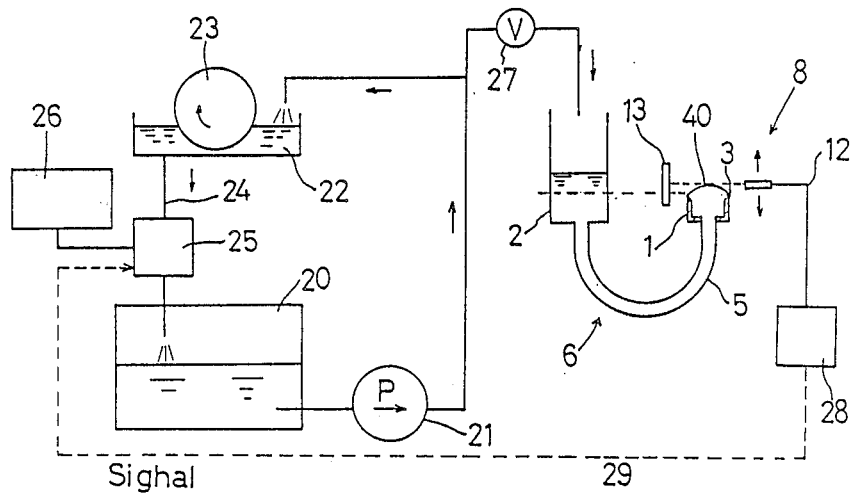

1

SURFACE TENSIOMETER AND CONCENTRATION CONTROLLING DEVICE

BACKGROUND OF THE INVENTION (1) Field of the Invention

The present invention relates to a surface tensiometer and a surface tension measuring method and also to a concentration controlling device and method utilizing the surface tensiometer and the surface tension measuring method, and more paticularly to a device or method of measuring or controlling concentraion of a liquid by measuring the concentration as a surface tension of the liquid, the device and the method being used for e.g. measuring alcohol concentration of a fountain solution used in an offset printing machine or a concentration of other kinds of water solution.

(2) Description of the Prior Art

A device for controlling concentration of fountain solution (alcohol water solution) for use in e.g. an offset printing machine is known from a prior-art reference U.S. Pat. No. 3,848,618.

The device of this reference invention essentially comprises a U-tube formed by connecting lower portions of two cylinders with a narrow pipe, with one of the cylinders being preliminarily filled with a reference water solution and the other cylinder being gradually and continuously filled with the fountain solution. The surface of the reference water solution is vertically moved in accordance with a specific gravity of the fountain solution. Further, the cylinder containing the reference solution attaches at a predetermined position thereof an electrode for detecting the surface of the reference water solution. Thus, by detecting the surface of the reference water solution by this electrode, a difference between the specific gravities of the fountain solution and the reference solution is measured, which measured difference is utilized consequently for controlling alcohol concentration of the fountain solution.

However, with the above device, since the control-object fountain solution need be continuously fed into the cylinder, there occurs the problem of considerable soiling of the U-tube or the electrode by contaminant present in the fountain solution in direct proportion to the feeding amount of the control-object solution. Further, since the liquid surface of the reference water is not sufficiently stabilized, this prior-art device is incapable of accurate measurement of the specific gravity of control-object solution. Moreover, the device has the disadvantage of its complicated construction which makes its cleaning operation difficult.

In view of the above-described state of the art, the primary object of the present invention is to provide a device and a method for readily, reliably and accurately measuring a surface tension of a liquid, the device and method eliminating the necessity of continuous feeding of the liquid.

A further object of the present invention is to provide a device and a method for controlling concentration of a liquid which surface tension value varies in proportion to its concentration.

SUMMARY OF THE INVENTION

In order to accomplish the above-noted primary object, a surface tensiometer related to the present invention comprises: a measurement container having its upper edge opened along a horizontal perpendicular plane to its axis with its lower open end communicating with an end of a connecting pipe; an inlet container having its upper edge opened at a position higher than the upper edge of the measurement container communicates with the opposite end of the connecting pipe; and measuring means for measuring the height of a highest position of a convex liquid surface or meniscus by the liquid in a measurement container in an equilibrium between an upward force exerted by a pressure difference between the liquid in the inlet container and on the liquid in the measurement container due to height difference between the surface of the liquid in the inlet container compared with the surface of the liquid raised from the opened upper edge of the measurement container. The measurement is made after the liquid introduced from the inlet container reaches the upper edge of the measuement container and overflows from the measurement container and stops flowing to form a liquid convex surface above the end 3 of the inlet container which is caused by a downward force exerted by a surface tension of the surface of the raised liquid; and away from said face end of said stepped, cylindrical housing;

Further according to a surface tension measuring method using the above surface tensiometer of the present invention, comprises the steps of: introducing a measurement-object solution into the inlet container; and measuring by the measuring means a surface tension of the measurement-object solution through a measurement of a highest point of a convex solution surface formed upwardly from the opened upper edge of the measurement container, the convex surface being formed after the introduced solution overflows from an opening of the upper edge of the measuring container.

In order to accomplish the second object, a concentration control device related to the present invention comprises: a measurement container having its upper edge opened horizontally and communicated with an end of a connecting pipe; an inlet container having its upper edge opened at a position higher than the upper edge of the measurement container and communicated with the opposite end of the connecting pipe at a position lower than the upper edge of the measurement container; a liquid-surface detecting sensor having a detecting section for detecting a convex liquid surface statically formed in an equilibrium between an upward force exerted by a pressure difference due to a height difference between a liquid surface of the measurement container with the liquid surface being raised from the opened upper edge of the measurement container after the liquid introduced from the inlet container reaches and overflows from the measurement container and a liquid surface of the inlet container and a downward force exerted by a surface tension of the raised liquid surface of the control-object solution per se, detecting section being placed at a desired position on a vertical axis extending through the position of the highest point of the convex liquid surface; a gauge operatively connected with the liquid-surface sensor for displaying a height of the detecting section; and adjusting means for adjusting a concentration of a control-object solution at a fixed value by utilizing the detection of the convex liquid-surface detected by the detecting section.

A concentration control method using the concentration control device of the present invention comprises the steps of: fixedly positioning the detecting section for detecting a liquid surface at a desired position on the vertical axis; introducing a control-object solution into the inlet container; adjusting to a predetermined value by adjusting means a concentration of the control-object solution through a detection by the detecting section of the convex solution surface formed forwardly from the opened upper edge of the measurement container, the convex surface being formed after the introduced solution overflows from an opening of the upper edge of the measuring container.

Functions of the above features will be described next with reference to FIG. 2. Incidentally, the height difference between the liquid surfaces is exaggeratedly illustrated in this drawing for facilitating the understanding of the principle of the invention.

As shown in FIG. 2(a), when more than a predetermined amount of a measurement-object liquid is introduced into an inlet container 2, the liquid passes through a connecting pipe 5 to reach a measurement container 1 and overflows from an upper edge of this measurement container 1. After the introduction of the liquid is stopped, the overflowing speed of the liquid from the upper edge of the measurement container 1 gradually decreases with a decrease of a head h1 of the liquid in the inlet container 1. Consequently, as shown in FIG. 2(b), the liquid flow is stabilized as forming a convex liquid surface 40 having a certain height h2 measured from the upper edge of the measurement container 1. Referring more particularly to this convex liquid surface 40, the surface 40 is formed convex because of the surface tension of the liquid per se and at the same time formed with its highest point being statically positoned lower than the liquid surface in the inlet container 2 by a height difference of h0. By measuring the height h2 of the highest point of the concave liquid surface 40 statically formed in the measurement container 1, it is possible to measure the surface tension of the liquid very accurately. That is, in FIG. 2(b), if the surface tension of the liquid is T, then we obtain:

$$T = f(h2, h0), \quad h0 = g(h2)$$

Accordingly, by measuring the height h2 of the highest point of the convex liquid surface 40 formed upwardly from the upper edge 3 of the measurement container 1, it becomes possible to measure the surface tension as a unit of length. Further, if the liquid has such concentration as varies in proportion to its surface tension, a measurement of this concentration becomes also possible through the above measurement of the surface tension.

Moreover, as shown in FIG. 3 and FIG. 9, if there is provided a fixed liquid-surface sensor 8 having a detecting line Z which is tangential to the curved convex surface at X for detecting the convex liquid surface 40 of a liquid having a specific concentration, and adjusting means for adjusting the concentration of the liquid by utilizing the detection result of sensor 8, it becomes possible to control the liquid concentration at a predetermined or desired value by adjusting the concentration until the convex surface first touches the line Z.

As described above, according to the present invention, the measurement-object liquid needs to be supplied into the measurement device only all at one time when a measurement is needed, and such continuous supply of the liquid as required by the prior-art devices is no longer necessary. As the result, the soiling of the device occurs much less, and the measurement of a surface tension or a concentration of liquid may be carried out in a short time. Also, since the measurement is effected on the stabilized liquid surface, the device may provide very reliable data and adjustment of the device is facilitated as well. Furthermore, the device has the advantage of its simple construction which facilitates cleaning operation and reduces its running costs.

Further and other features, functions and advantages of the present invention will become apparent from the following more detailed description of the invention with reference to the accompanying drawings.

BRIEF DESCRIPTION OF THE DRAWINGS

FIGS. 2(a) and 2(b) are schematic vertical sections of a U-tube illustrating a principle of the surface tensiometer of the present invention, FIG. 3(a) is a vertical section of major portions of the tensiometer of FIG. 1, FIG. 3(b) is a plane view of the major portions of the tensiometer of FIG. 1, FIG. 4 is a vertical section of major portions of a liquid-surface detecting sensor according to a further embodiment of the present invention, FIG. 5 is a vertical section showing major portions of a measurement container upper edge of the surface tensiometer of FIG. 1, FIG. 6 is a schematic vertical section of the U-tube showing a stabilized condition of the surface tensiometer of the invention, FIG. 7 is a schematic view of an embodiment of a further liquid-surface detecting sensor of the surface tensiometer of the invention, FIG. 9 is a schematic view of a concentration control device utilizing the surface tensiometer for controlling IPA concentration of a fountain solution for use in an offset printing machine.

DESCRIPTION OF THE PREFERRED EMBODIMENTS

Preferred embodiments of the present invention will be particularly described hereinafter with reference to the accompanying drawings.

Figure 1A:
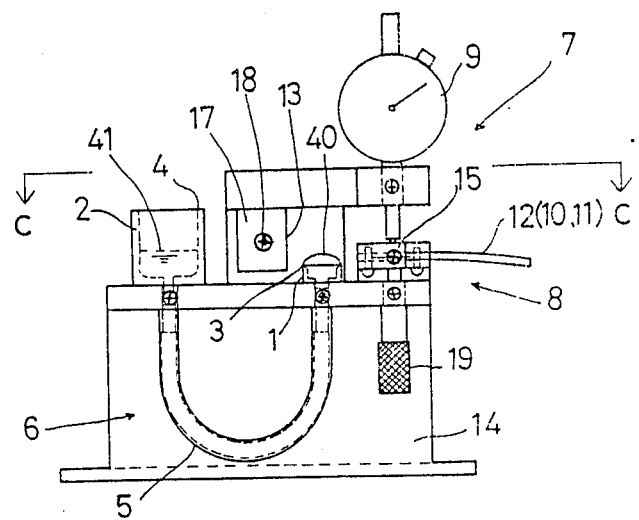
FIGS. 1(a), 1(b) and 1(c) show a preferred embodiment of a surface tensiometer related to the present invention, with FIG. 1(a) being a front view, FIG. 1(b) being a side view and FIG. 1(c) being a perspective view taken along a line C—C of FIG. 1(a), respectively.
Figure 1:
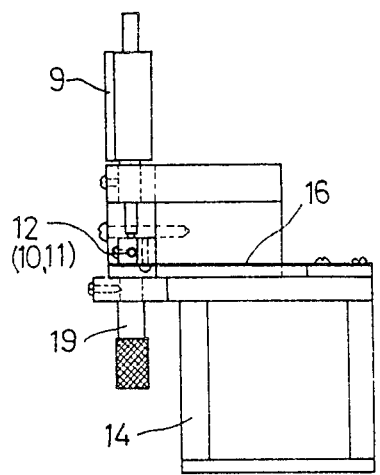
Figure 1:
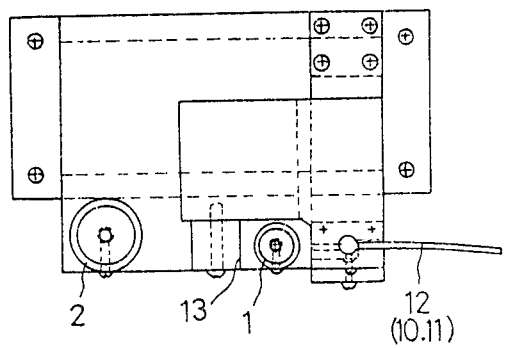

A surface tensiometer related to the present invention, as shown in FIG. 1, comprises a U-tube 6, a liquid-surface detecting sensor 8, a gauge 9 and a body 14. The U-tube 6 includes a measurement container 1, an inlet container 2 and a connector pipe 5.

As shown in FIG. 3, the measurement container 1, which is utilized for measuring a surface tension of a measurement-object solution, is formed as a cylindrical container having a horizontally opened upper edge 3. It is essential that the measurement container 1 have such a configuration as to prevent formation of bubbles therein when the solution is introduced thereinto. In this container, there is formed a liquid surface 40 which should be convex approximately spherical face appropriate for measurement. If the measurement-object solution comprises such alcohol water solution as isopropanol alcohol (to be referred to as 'IPA' hereinafter), it is preferred for obtaining such approximately spherical liquid surface that the upper edge 3 of the measurement container 1 be substantially circular with a diameter D not exceeding 15 mm. For, if this diameter exceeds the value, the liquid surface 40 is formed flat at its center and such a flat surface is not appropriate for measurement. Incidentally, aside from the above-noted circular shape, the upper edge 3 may be also formed to be an oval shape, an annular shape having a pair of opposite sides substantially parallel to each other, or a multi-side shape. The selection of this shape should be made depending on characteristics of the measurement-object solution and manufacturing conditions of the measurement container.

The surface tension phenomenon take place at a contact point between the upper edge and the solution. Thus, the upper edge 3 on the upper end of the measurement container is formed by an acute-angular vertical cross section. More specifically, this acute-angular vertical cross section may be sloped downwardly from the outer side of the inner side of the container as shown in FIG. 3a, or may be sloped downwardly from the inner to the outer side of the same as shown in FIG. 4, or may be sloped downwardly towards the inner and outer sides of the container as shown in FIG. 7. In the case of shape in FIG. 3a where the edge is sloped from the inner to the outer side of the container, it is preferable that a sloped face 3a1 of the upper edge and the horizontal surface form an angle $\alpha$ not exceeding 45 to 60 degrees.

As shown in FIG. 5, a top portion 3d of the upper edge should be formed most preferably as a sharpened blade. In fact, due to the limit of the manufacturing precision of the same, this top portion 3d has a horizontal face 3d1 with an extremely short width as shown in FIG. 5(a). Incidentally, it is preferred that the width t of the horizontal face 3d1 be less than 0.2 mm. Further as shown in FIG. 5(b), the top portion 3d further includes a curved face 3d2 with an extremely small curvature radius.

As described hereinbefore, the convex liquid surface 40 is formed at the upper edge 3. Accordingly, if this portion is soiled, there occurs errors in the measurement. For this reason, in measuring a water solution, if at least a peripheral surface of the upper edge 3 of the measurement container 1 is formed by copolymer such as vinyl fluoride, ethylene trifluoride, vynylidene fluoride or propylene hexafluoride, the upper edge will obtain good water-repelling characteristics which may advantageously reduce the measurement error. Needless to say, the entirety of the measurement container 1 may be formed of such material. The measurement values obtained by this surface tensiometer vary relative to the kind of the measurement-object solution and the material forming the measurement container 1. However, accurate measurement is possible by corresponding the measurement value to the highest point of the convex liquid surface 40 as long as the case measurement-object solution is used.

With the above-described arrangements, the convex liquid surface 40 may be reliably formed spherically from the upper edge 3 with its portion substantially centrally of the container 1 being highest in the altitude.

As shown in FIG. 1, the inlet container 2 for receiving the measurement-object solution is formed as a cylindrical container having an opened upper edge 4. As is the case with the measurement container 1, this inlet container 2 should be so formed as to prevent formation of bubbles when the measurement-object solution is introduced thereinto. Also, in order to stabilize overflow of the measurement-object solution by a "head" as will be described later, it is preferred that the inlet container 2 have a larger capacity that the measurement container 1. The inlet container open upper edge 4 is positioned at a higher altitude than the upper edge 3 of the measurement container 1. Also, the inlet container 2 is communicated with the opposite end of the connecting pipe 5 at a position lower than the measurement container upper edge 3. Accordingly, the convex liquid surface 40 formed from the upper edge 3 of the measurement container 1 comes into equilibrium with a liquid surface 41 formed in the inlet container 1 at a position higher than the connecting position between the inlet container 2 and the connecting pipe 5. Incidentally, depending on the setting position of the measurement container 1, the liquid surface 41 of the inlet container 2 may be formed inside the connector pipe 5. In such case, the connecting pipe portion forming this liquid surface 41 may substitute the inlet container 2. However, for accurate measurement it is preferrd that the liquid surface 41 be formed inside the inlet container 2.

The connecting pipe 5 is constituted by a transparent tube member formed of a flexible synthetic resin material. The material container 1 and the inlet container 2 respectively have adjacent a lower end thereof a cylindrical connecting member downwardly projecting therefrom and defining a connecting hole 1a for engaging a free end of the connecting pipe 5. If the connecting pipe 5 is formed of a transparent material as described above, it is possible, as shown in FIG. 4, to visually inspect bubbles which may be formed and retained adjacent the connecting hole 1a. Also, if the pipe 5 is formed of a flexible material, such bubbles may be conveniently removed by pinching the pipe 5. Further, as shown in FIG. 3(a) if the lower edge of the connecting member is formed with a slope extending upwardly from the inside to the outside thereby forming stepless the interior of the lower edge, such formation and retention of bubbles may be advantageously reduced. Also, such stepless interior construction may be obtained by forming all or two of the connecting pipe 5, the measurement container 1 and the inlet container 2.

Incidentally, if the connecting hole 1a is defined adjacent the lowermost portions of the measurement container 1 and the inlet container 2, when the measurement-object solution is introduced into the inlet container 2, the solution is discharged with a sufficient force from the bottom of the measurement container 1 via the connecting pipe 5, whereby the measurement-object liquid inside the U-tube 6 may be well replaced and a sampling may be effected reliably.

As shown in FIG. 1, the measurement container 1 and the inlet container 2 are respectively detachably attached by securing means such as screws to the same horizontal face of the body 14. Therefore, simply by detaching the connecting pipe 5, the measurement container 1 and the inlet container 2 therefrom, the body 14 may be readily cleaned. Incidentally, for an ordinary use, the cleaning should be made on a vicinity of the upper edge 3 which affects the measurement precision most significantly.

As shown in FIG. 3, a beam emitting/receiving optical fiber 12 is employed as the liquid-surface detecting sensor 8 for detecting the position of the highest point of the convex liquid surface 40 formed in the measurement container 1. This optical fiber 8 has a double construction including a beam emitting element and a beam receiving element disposed coaxially with each other. The beam emitted from the beam emitting element is vertically reflected by a mirror 13 to be received by the beam receiving element. Also, though not shown, at the opposite end of this beam emitting/receiving optical fiber 12, there are provided a beam emitting device for the beam emitting element and a beam receiving device for the beam receiving element, respectively. The beam receiving device is operable to generate a signal depending on whether the received beam amount is below a predetermined value or not. This device per se is well-known and is operable to detect presence or absence of an object on an optical path of the projected beam travelling from the beam emitting element to the beam receiving element. In this embodiment, by utilizing the above function, the position of the highest point of the convex liquid surface 40 is detected. More particularly, if the predetermined value of the beam amount to be received by the beam receiving device is adjustably set as a value obtained when the optical path Z substantially comes into contact with the highest point of the convex liquid surface 40, the position substantially corresponding to this highest point of the convex liquid surface may be detected. As described hereinbefore, the beam emitting/receiving optical fiber 12, the beam emitting device and the beam receiving device may comprise the conventional types.

Where the upper edge 3 has a circular periphery, the position of the highest point of the convex liquid surface 40 is substantially centrally of the measurement container 1 on the horizontal plane. Accordingly, as shown in FIG. 3, a detecting section X of the fiber for detecting the position of the highest point of the convex liquid surface 40 needs to be positioned on a vertical axis Y extending through the center of the measurement container 1. An end of the beam emitting/receiving optical fiber 12 and the mirror 13 are positioned opposed to each other across the convex liquid surface 40 formed from the upper edge of the measurement container 1 such that the optical path Z crosses the vertical axis Y with the path Z being maintained horizontal. With this arrangement, the detecting section X for detecting the position of the highest point of the convex liquid surface 40 is placed at a crossing point between the vertical axis Y and the optical path Z. In order to maintain this posture, the beam emitting/receiving optical fiber 12 is attached to the body 14 while being downwardly urged by an optical fiber holder 15 and plate spring 16. Under this optical fiber holder 15, there is provided a vertically adjustable screw 19 for lifting up the holder 15 in accordance with a rotational amount of a knob. With this arrangement and the downward urging force by the plate spring 16, it is possible to substantially vertically move the beam emitting/receiving fiber 12 with a high precision. The mirror 13 is attached to the body 14 by a mirror jig 17 so as to constantly maintain a vertical posture relative to the optical path Z of the projection beam emitted from the beam emitting element to be received by the beam receiving element. Accordingly, the projection beam emitted from the optical fiber 12 is reflected by the mirror 13 to be received by the optical fiber 12 as long as the projection beam is not interfered by the convex liquid surface 40. The mirror jib 17 is fixed to the body 14 by a mirror fixing screw 18. If the current posture of the mirror 13 is improper, the mirror fixing screw 18 is released for turning the mirror jig 17 whereby a fine adjustment of the mirror 13 is possible.

In operation, by vertically moving the detecting section X substantially along the vertical axis Y while maintaining the optical path Z horizontal by turning the adjusting screw 19, the position of the highest point of the convex liquid surface 40 may be reliably detected.

Incidentally, the beam emitting element and the beam receiving element need not necessarily be disposed coaxially in the same optical fiber 12. Instead, as shown in FIG. 4, it is possible to eliminate the mirror 13 and to provide a beam emitting optical fiber 10 and a beam receiving optical fiber 11 at opposite positions across the convex liquid surface 40 formed from the upper edge of the measurement container 1 such that the optical path Z being maintained horizontal crosses the vertical axis Y. In this case, however, the detection of the highest point must be carried out while correlating the movements of the beam emitting optical fiber 10 and the beam receiving optical fiber 11 so as to maintain the optical path Z horizontal. Also, the optical fiber is employed as the beam emitting/receiving unit in this embodiment. However, it is possible to employ a spot light source if the same is provided with an appropriate amount of orientation.

Figure 8:
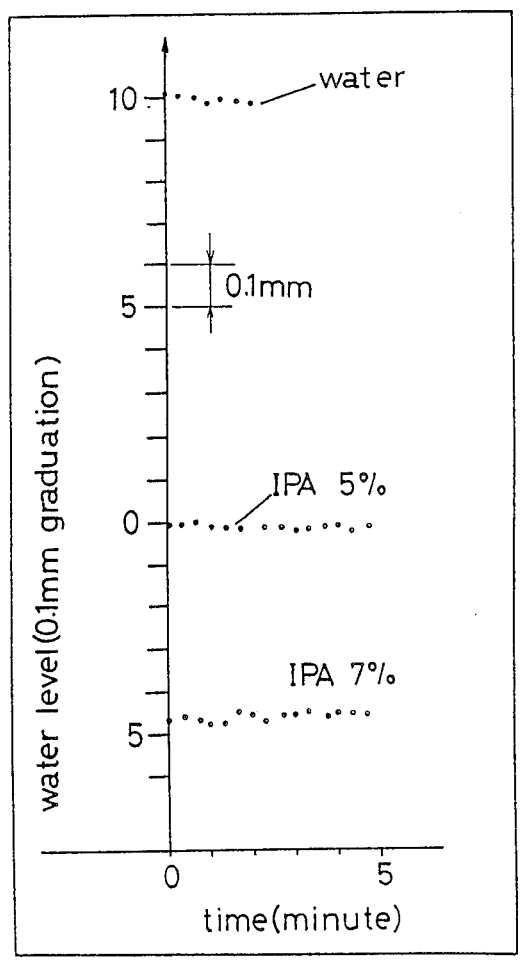
FIG. 8 is a graph illustrating results of surface tension measurements effected by the surface tensiometer of FIG. 1.

As shown in FIG. 1, the gauge 9 comprises a dial gauge and this gauge 9 is secured to the body 14 upwardly of the optical fiber holder 15. As the detecting element disposed downwardly thereof is placed in contact with the optical fiber holder 15, it is possible to measure the height of this holder 15, i.e. the height of the detecting section X. Consequently, the surface tension of the measurement-object liquid may be measured as a unit of length. For measuring the height of the highest point of the convex liquid surface 40 formed by the surface tension, it is possible to utilize the upper edge 3 of the measurement container 1 as a reference point. In place of this, it is possible to use an arbitrary point as the same as shown in FIG. 8. Incidentally, if the tensiometer of the present invention is used for measuring IPA concentration, a very small altitude difference such as some milimeters is significant for the measurement. For this reason, it is preferred that the dial gauge be of a high precision type capable of measuring by the unit of 1/100 mm. Further, as a substitute for the dial gauge, it is also possible to attach a scale for indicating a movement amount to the liquid-surface detecting sensor 8.

The body 14 is formed of a hard material such as steel or hard chloroethene polypropylene for reducing errors by distortion of the body 14 per se. Incidentally, though not shown, a spirit level and an anti-vibration device are attached to this body 14 for reducing measurement errors resulting from environmental factors.

Next, the steps of a surface tension measuring method utilizing the above-described surface tensiometer of the present invention will be particularly described with reference to FIGS. 1 and 2.

First, the measurement-object solution is sampled and a predetermined amount of the sample solution is introduced into the inlet container 2, so that the solution passes through the connecting pipe 5 to overflow from the upper edge 3 of the measurement container 1.

Second, when the inlet container is filled with the solution while the same overflowing from the upper edge 3 of the measurement container 1, the introduction of the solution is stopped. Thereafter, the liquid surface 41 in the inlet container 2 gradually reduces and the overflow from the upper edge 3 of the measurement container 1 is caused thereafter by a head h1 between the liquid surface 41 and the upper edge 3. The flow speed by the head h1 is about $\overline{2gh1}$ and, as shown by $\overline{h1}$ of this expression, this flow speed gradually decreases as the liquid surfaces come closer to the equilibrium. Therefore, the overflow condition immediately before the formation of the liquid surface 40 is substantially constant and regular regardless of the specific gravity of the measurement-object solution.

Within about several or ten seconds after the introduction, the measurement-object solution becomes still with forming a convex liquid surface from the upper edge 3, with which the sampling is completed. This liquid surface at the upper edge 3 has a convex and approximately spherical face due to the surface tension of the solution, and its downwardly reducing pressure by the surface tension comes into equilibrium with the upwardly-lifting pressure by the head: h0 +h2 in the inlet container 2 positioned at a higher altitude than the head h2 extending from the upper edge 3. In this static equilibrium, the altitude of the concave liquid surface 40 is very stable. That is, as shown in FIG. 6, if the liquid surface 41 in the inlet container 2 is slightly depressed to form a lower liquid surface 41', the convex liquid surface 40 in the measurement container 1 becomes a higher convex liquid surface 40'. A curvature radius of this convex liquid surface 40' is smaller than that of the liquid surface 40. With this reduced curvature radius, the inner pressure acting on the convex liquid surface 40' increases thereby lifting up the liquid surface 41' in the inlet container 2. On the other hand, if the liquid surface 41 in the inlet container 2 is slightly lifted up, similarly in the previous case, a downwardly depressing force will act on the liquid surface 41 in the inlet container 2. With balancing effect between these forces, the altitude of the convex liquid surface 40 may be very stable.

Third, the position of the highest point of the convex liquid surface 40 is detected and measured by moving the beam emitting/receiving optical fiber 12. Incidentally, if the beam emitting/receiving optical fiber 12 is moved to a higher altitude than the highest point of the convex liquid surface 40 prior to the above detection, the projection beam emitted from the base emitting device through the optical fiber 12 passes above the convex liquid surface 40 and is reflected by the mirror 13 to be received by the beam receiving device, whereby no signal is generated. As the optical fiber 12 is moved downwardly by turning this adjusting screw 19, the projection beam emitted through the optical fiber 12 is interferred by the highest point of the convex liquid surface 40 and does not return to the beam receiving device, upon which the beam receiving device generates a signal for indicating the detection of the highest point of the convex liquid surface 40. If an operator reads a value on the dial gauge 9 when this signal is being emitted, he may readily measure the position substantially corresponding to the highest point of the convex liquid surface 40.

Incidentally, as shown in FIG. 4, if the connecting pipe 5 retains some air bubbles therein, an accurate measurement is not possible. In this case, the above-described processes should be repeated from the beginning after pinching the pipe 5 for removing the bubbles therefrom.

The results of surface tension measurement operation using the above processes and conducted for comparing an IPA water solution and water are illustrated in FIG. 8. As shown, the positions of the highest points of the convex liquid surface 40 are fairly distinguishable between the water and the IPA water solution. Accordingly, it was proved that the method of the present invention may provide very reliable measurement data.

Next, a further embodiment of the surface tensiometer related to the present invention will be particularly described with reference to FIG. 7.

In the previous embodiment, the optical fiber is employed for detecting the concave liquid surface 40. In this embodiment, however, an electrode which is an example of electrical detecting means is employed instead. This electrode denoted by a reference numeral 30 is attached to an end of an arm 32 with a vertical height thereof being adjustable by means of an adjusting screw 31. The other end of the arm 32 is pivotably attached to the body by a support mechanism 33. A detecting device 34 is electrically connected with the electrode 30 and a grounding 35 placed into contact with the measurement-object solution inside the measurement container 1. In case the detecting device 34 is a type detecting a current conduction, the detection of the convex liquid surface 40 is effected as the electrode 30 comes into contact with the convex liquid surface 40 to sense the current conduction. On the other hand, if the detecting device 34 is a type detecting a potential variation, the same is effected in a non-contact manner as the electrode 30 comes within a predetermined range from the convex liquid surface 40 to sense the potential variation. These electrical detecting means of the current-conduction detecting type and the potential variation-detecting type may be constituted by the conventional devices.

For measuring a surface tension or adjusting a concentration of the measurement-object solution utilizing the above-described measuring device of this embodiment, first, the electrode 30 is temporarily set to a side of the measurement container 2 prior to the introduction of the measurement-object solution. Second, after the introduced solution overflows from the upper edge of the measurement container 1 with forming a liquid surface therefrom, the support mechanism 33 is pivoted to place the electrode 30 onto the vertical axis Y of the measurement container 1. With this arrangement, the electrode 30 is placed out of contact with the measurement-object solution except for measurement or control operation. Incidentally, the electrode 30 need not be pivoted laterally but may be moved vertically instead.

Next, a concentration control operation using the surface tensiometer of the present invention will be described with reference to FIG. 9.

In this case, a control-object solution comprises an IPA water solution which is a fountain solution for use in an offset printing machine.

Generally, a fountain solution recycling apparatus for an offset printing machine is constructed as described as follows: The fountain solution reserved in a tank 20 is forcibly drawn by a recycling pump 21 to a fountain-solution pan 22 to wet a water fountain roller 23. Then, the solution is recycled via an exhaust passage 24 to the tank 20. In the course of the exhaust passage 24, there is provided a mixer 25 which is operable, when receiving a signal, to add IPA reserved in an IPA tank 26 to the fountain solution thereby maintaining the IPA concentration of the solution constant.

First, the beam emitting/receiving optical fiber 12 is moved to a position corresponding to a predetermined value on the dial guage by turning the adjusting screw 19, such that the detecting section X is fixed as a predetermined altitude. Second, by operating a sampling valve 27, a predetermined amount of the fountain solution is sampled into the inlet container 2 for forming the concave liquid surface 40 at the opening of the upper edge 3 of the measurement container 1. As the valve 27 is adapted to be automatically closed or opened only for a predetermined time period, a predetermined amount of the fountain solution is fed constantly. In the IPA concentration is low, as shown in FIG. 8, the concave liquid surface 40 has a higher height because of increased surface tension. If this height of the convex liquid surface 40 is higher than the position of the fixedly set detecting section X, the projection beam is interferred by the surface 40 and the beam emitting-/receiving device 28 generates a signal 29. Judgement on whether or not to generate this signal 29 is effected at the first moment when the energized beam emitting-/receiving device 28 emits the projection beam. Thereafter, the beam-emitting or beam-nonemitting condition is maintained until the beam emitting/receiving device 28 is reset. Accordingly, the beam emitting or non-emitting condition is not subjected to vertical fluctuations of the convex liquid surface due to vibrations or the like.

Further, it is also possible to operatively connect the valve 27 and the beam emitting/receiving device 28 such that the device 28 is automatically energized upon closing of the valve 27. Also, it is possible to attach a delay timer to the beam emitting/receiving device 28 for delaying its beam projection. With this, the device 28 is inhibited from its beam projecting operation for a few seconds after its energization. In this case, the liquid-surface surface sensor 8 may effect a more accurate measurement after the concave liquid surface 40 is sufficiently stabilized. The above arrangements are very advantageously since the series of control operations may become automatic.

Incidentally, if the above-described automatic valve 27 and the automatic beam emitting/receiving device 28 are employed and the detecting section X is fixedly placed at a predetermined position, the device may be used as a concentration measuring device for judging only whether the IPA concentration is above a predetermined value or not.

The above signal 29 is received by the mixer 25 and the mixer 25 adds a predetermined amount of IPA reserved in the IPA tank 26 to the fountain solution so as to adjust its IPA concentration to a predetermined value. On the other hand, if the IPA concentration is higher than the predetermined value, the height of the convex liquid surface 40 is lower than the fixed position of the optical fiber 12. Accordingly, the projection beam is not interferred by the liquid surface 40 and the addition of IPA to the solution is not carried out. Also, in this case, the IPA concentration is automatically adjusted to the predetermined value because of gradual evaporation of the IPA content. If a sampling operation of the fountain solution with using the above-described device, it becomes possible to maintain IPA concentration of the fountain solution constant.

Figure 10:
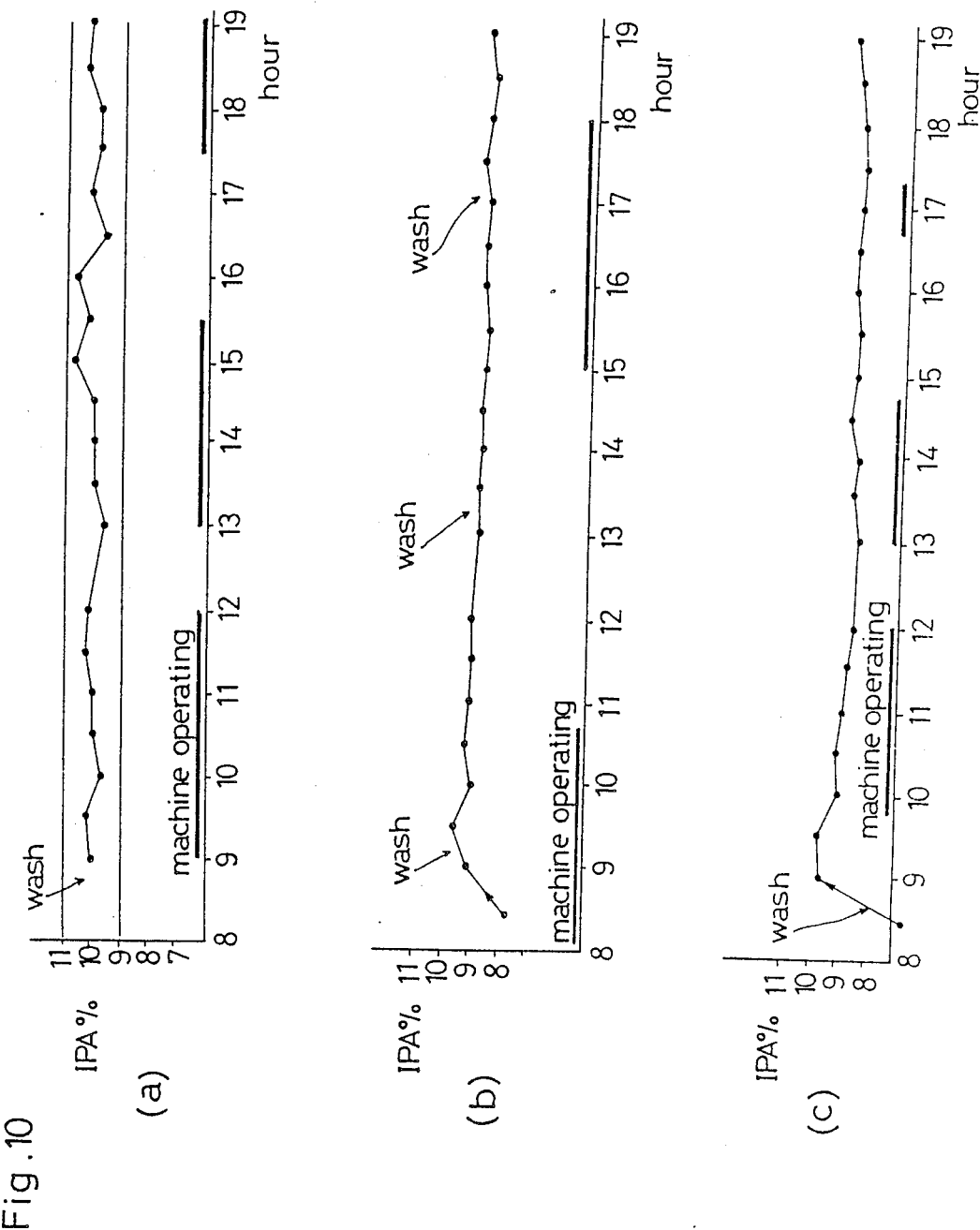
FIGS. 10(a), 10(b), and 10(c) are graphs showing results of concentration control effected by the concentration control device of FIG. 9.

FIGS. 10(a), 10(b) and 10(c) show results of IPA concentration control operations of a fountain solution used in an offset printing machine, each showing results of operations conducted on different dates. Incidentally, bold lines in the drawings denote operations of the offset printing machine and a character "wash" denotes a washing or cleaning operation of the upper edge 3 of the measurement container 1. Statistically processed values of these measurement operations are shown in Table 1 below.

TABLE 1

| graph in FIG. 11 | IPA concentration of fountain solution of offset printing machine | | |
|---|---|---|---|
| | (a) | (b) | (c) |
| measurement number n | 20 | 20 | 20 |
| average value X of concentration | 10.07 | 8.98 | 8.97 |
| standard deviation $T_{n-1}$ | 0.3028 | 0.2706 | 0.3450 |

As may be seen from the above measurement values, it is possible for the measuring device of the present invention to control IPA concentration of fountain solution very accurately.

Incidentally, in the above embodiment, the liquid surface rises with the evaporation of IPA solute. However, if a non-evaporating type solute is used, the concave liquid surface 40 falls due to evaporation of the water content. In this case, the same control operation is possible if additional water is supplied in response to a signal emitted when the projection beam is not interferred.

What is claimed is:

1. A surface tensiometer comprising:
   a measurement container (1) having an upper edge (3) on an upper end thereof opened on a horizontal plane perpendicular to an axis of said measurement container with its lower end communicating with an end of a connecting pipe (5);
   an inlet container (2) having an upper edge (4) thereof opened on a plane perpendicular to its axis located at a position higher than the upper edge (3) of said measurement container (1) with an open bottom edge that communicates with the opposite end of the connecting pipe (5); and
   measuring means (7) for measuring a height of a highest position of a convex liquid surface statically formed on said upper end of said measurement container when in an equilibrium between an upward force exerted by a pressure difference in said inlet container relative to the liquid in said measurement container due to a height difference between a liquid surface of a liquid in said inlet container and said measurement container (1), with the height of the concave liquid surface being raised from the opened upper edge (3) of said measurement container (1) after the liquid introduced into said inlet container (2) reaches and overflows from said measurement container (1) and then reaches said equilibrium.

2. A surface tensiometer, as defined in claim 1, wherein said upper edge (3) on the upper end of the measurement container (1) is formed by an acute-angular vertical cross section.

3. A surface tensiometer, as defined in claim 2, wherein said acute-angular vertical cross section of the upper end of said measurement container is sloped downwardly from the outer surface of the inner surface of the measurement container (1).

4. A surface tensiometer, as defined in claim 2, wherein a top portion (3d) of said upper edge (3) of the measurement container (1) has a flat face having an extremely small width.

5. A surface tensiometer, as defined in claim 1, wherein said measurement container (1), said inlet container (2) and said connecting pipe (3) are formed integrally as one.

6. A surface tensiometer, as defined in claim 1, wherein said connecting pipe (5) is detachably connected to said measurement container (1) and said inlet container (2).

7. A surface tensiometer, as defined in claim 6, wherein said connecting piper (5) is connected to said measurement container (1) and said inlet container (2) by outwardly engaging a bottom end of each container having a connecting hole (1a) defined respectively in said measurement container (1) and said inlet container (2), said bottom end of each container having a lower end with an acute-angular vertical cross section upwardly sloped from the inside to the outside.

8. A surface tensiometer, as defined in claim 1, wherein said upper edge (3) of the measurement container (1) has a circular periphery with a diameter not exceeding 15 mm.

9. A surface tensiometer, as defined in claim 1, wherein at least a peripheral surface of said upper edge (3) is formed of a water-repelling material.

10. A surface tensiometer as defined in claim 9, wherein said water-repelling material comprises a copolymer selected from the group consisting of vinyl fluoride, ethylene trifluoride, vynylidene fluoride and propylene hexafluoride.

11. A surface tensiometer, as defined in claim 1, wherein said measuring means (7) includes:
   a liquid-surface detecting sensor (8) having a detecting section X movable along a vertical axis Y extending through a position where the highest point of said convex liquid surface is formed upwardly when the opened upper edge of said measurement container (1); and
   a gage (9) is operatively connected with said liquid-surface sensor (8) for measuring a height of said convex liquid surface at detecting section X.

12. A surface tensiometer, as defined in claim 11, wherein said liquid-surface sensor (8) includes:
   a beam emitting element (10) for emitting a projection beam;
   a beam receiving element (11) for receiving the projection beam; and
   an optical path Z of the projection beam which travels from said beam emitting element (10) to said beam receiving element (11) crossing said vertical axis Y with the optical path Z being constantly maintained horizontal, said detecting section X being positioned at a crossing point between said vertical axis Y and said optical path Z, such that the position of said highest point of the convex liquid surface is detected as optical path Z is interferred by said convex liquid surface at the position of said detecting section X.

13. A surface tensiometer, as defined in claim 12, wherein said beam emitting element (10) and said beam receiving element (11) are positioned opposed to each other across said convex liquid surface formed from said upper edge (3) of the upper end of said measurement container (1).

14. A surface tensiometer, as defined in claim 12, wherein said beam emitting element (10) and said beam receiving element (11) are formed integrally as a beam emitting/receiving unit (12) opposed to said mirror (13) across said convex liquid surface.

15. A surface tensiometer, as defined in claim 11, wherein said detecting section X of the liquid-surface sensor (8) comprises an electrode (30) operable to electrically detect the position of the highest point of said convex liquid surface.

16. A surface tensiometer, as defined in claim 15, wherein said liquid-surface sensor (8) comprises a contact type electric sensor which electrode (30) detects the position of the highest point of said convex liquid surface by detecting a current conduction as coming into contact with said convex liquid surface.

17. A surface tensiometer, as defined in claim 15, wherein said liquid-surface sensor (8) comprises a non-contact type electric sensor which electrode (30) detects the position of the highest point of said convex liquid surface by detecting a potential variation as coming closer to said convex liquid surface.

18. A surface tensiometer, as defined in claim 16, wherein said electrode (30) is movable away from said convex liquid surface towards said measurement container (1) until the formation of said convex liquid surface.

19. A surface tensiometer, as defined in claim 11, wherein said gauge (9) comprises a dial gauge.

20. A surface tension measuring method using a surface tensiometer, as defined in claim 1, comprising the steps of:
   introducing a measurement-object solution into an inlet container (2); and
   measuring by a measuring means (7) a surface tension of the measure-object solution through a measurement of a highest point of a convex solution surface formed upwardly from an opened upper end having an upper edge (3) of said measurement container (1), said convex surface being formed after the introduction solution overflows from an opening of the upper edge (3) of said upper end of said measurment container (1).

21. A surface tension measuring method, as defined in claim 20, wherein said measuring means (7) includes:
   a liquid-surface detecting sensor (8) having a detecting section X movable along a vertical axis Y extending through a position where the highest point of said convex liquid surface is formed upwardly from the opened upper end having an upper edge of said measurement container (1); and
   a gauge (9) being operatively connected with said liquid-surface sensor (8) for measuring a height of said detecting section X.

22. A surface tension measuring method, as defined in claim 21, wherein said liquid-surface sensor (8) includes:
   a beam emitting element (10) for emitting a projection beam;
   a beam receiving element (11) for receiving the projection beam; and
   an optical path Z of the projection beam which travels from said beam emitting element (10) to said beam receiving element (11) crossing said vertical axis Y with the optical path Z being constantly maintained horizontal, said detecting section X being positioned at a crossing point between said vertical axis Y and said optical path Z, such that the position of said highest point of the convex liquid surface is detected as said optical path Z is interferred by said convex liquid surface at the position of said detecting section X.

23. A surface tension measuring method, as defined in claim 22, wherein said beam emitting element (10) and said beam receiving element (11) are formed integrally as a beam emitting/receiving unit (12) opposed to said mirror (13) across said convex liquid surface.

24. A concentration control device comprising:
a measurement container (1) having an upper edge (3) thereof on an opened end of said measurement container on a horizontal plane perpendicular to an axis of said measurement container (1), and a lower end that communicates with an end of a connecting pipe (5);
an inlet container (2) having an upper edge (4) thereof opened on a horizontal plane perpendicular to its axis at a position higher than the upper edge (3) of said measurement container (1) which communicates with the opposite end of said connecting pipe (5);
a liquid-surface detecting sensor (8) having a detecting section X for detecting a convex liquid surface statically formed in an equilibrium between an upward force exerted by a pressure difference in said inlet container due to a height difference between a liquid surface and said measurement container (1), with said liquid surface in said measurement container being raised from the upper edge (3) of said measurement container (1) after the control-object solution introduced from said inlet container (2) reaches and overflows from said measurement container (1) and the liquid surface of said measurement container (1) reaches an equilibrium, said detecting section X being placed at a desired position on a vertical axis Y extending through the position of the highest point of the convex liquid surface;
a gauge (9) is operatively connected with said liquid-surface sensor (8) for displaying a height of said detecting section X; and
adjusting means (25) for adjusting a concentration of a control-object solution at a fixed value by utilizing the detection of the convex liquid-surface detected by said detecting section X.

25. A concentration control device, as defined in claim 24, wherein said adjusting means (25) comprises a mixer operable to automatically add to the control-object solution a predetermined amount of a solvent of a solute of the control-object solution upon detection of the convex liquid surface by said detecting section X.

26. A concentration control device, as defined in claim 24, wherein said liquid-surface sensor (8) includes:
a beam emitting element (10) for emitting a projection beam;
a beam receiving element (11) for receiving the projection beam; and
an optical path Z of the projection beam which travels from said beam emitting element (10) to said beam receiving element (11) crossing said vertical axis Y with the optical path Z being constantly maintained horizontal, said detecting section X being positioned at a crossing point between said vertical axis Y and said optical path Z, such that the position of said highest point of the convex liquid surface is detected as said optical path Z is interferred by said convex liquid surface at the position of said detecting section X.

27. A concentration control device, as defined in claim 26, wherein said beam emitting element (10) and said beam receiving element (11) are formed integrally as a beam emitting/receiving unit (12) opposed to said mirror (13) across said convex liquid surface.

28. A concentration control method using a concentration control device, as defined in claim 24, comprising the steps of:
fixedly positioning said detecting section X for detecting a liquid surface at a desired position on said vertical axis Y;
introducing a control-object solution into said inlet container (2); and
adjusting to a predetermined value by adjusting means (25), a concentration of the control-object solution through a detection by said detecting section X of said convex solution surface formed upwardly from an opened upper edge (3) of a measurement container (1), said convex surface being formed after the introduced solution overflows from an opening of the upper edge (3) of said measurement container (1) and reaches an equilibrium.

29. A concentration control method, as defined in claim 28, wherein said adjusting means (25) comprises a mixer operable to automatically add to the control-object solution a predetermined amount of a solvent or a solute of the control-object solution upon detection of the convex liquid surface by said detecting section X.

30. A concentration control method as defined in claim 29, wherein said control-object solution comprises a fountain solution for use in an offset printing machine, alcohol concentration of said fountain solution being controlled at a predetermined value.

31. A concentrate control method, as defined in claim 28, wherein said liquid-surface sensor (8) includes:
a beam emitting element (10) for emitting a projection beam;
a beam receiving element (11) for receiving the projection beam; and
an optical path Z of the projection beam which travels from said beam emitting element (10) to said beam receiving element (11) crossing said vertical axis Y with the optical path Z being constantly maintained horizontal, said detecting section X being positioned at a crossing point between said vertical axis Y and said optical path Z, such that the position of said convex liquid surface is detected as said optical path Z is interferred by said convex liquid surface at the position of the detecting section X.

32. A concentration control method, as defined in claim 31, wherein said beam emitting element (10) and said beam receiving element (11) are formed integrally as a beam emitting/receiving unit (12) opposed to said mirror (13) across said convex liquid surface.

* * * * *